United States Patent
Jacobs et al.

(10) Patent No.: US 11,890,385 B2
(45) Date of Patent: Feb. 6, 2024

(54) BIOMEDICAL FOAM

(71) Applicant: Stryker European Holdings I, LLC, Kalamazoo, MI (US)

(72) Inventors: Johannes Jacobus Jacobs, Cork (IE); Colin Stanley, Crosshaven (IE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 498 days.

(21) Appl. No.: 16/955,437

(22) PCT Filed: Dec. 20, 2018

(86) PCT No.: PCT/IB2018/060463
§ 371 (c)(1),
(2) Date: Jun. 18, 2020

(87) PCT Pub. No.: WO2019/123389
PCT Pub. Date: Jun. 27, 2019

(65) Prior Publication Data
US 2021/0121598 A1 Apr. 29, 2021

Related U.S. Application Data (60) Provisional application No. 62/608,256, filed on Dec. 20, 2017.

(51) Int. Cl.
*A61L 15/42* (2006.01)
*A61L 15/26* (2006.01)
*A61L 15/44* (2006.01)

(52) U.S. Cl.
CPC ............ *A61L 15/425* (2013.01); *A61L 15/26* (2013.01); *A61L 15/44* (2013.01); *A61L 2300/232* (2013.01); *A61L 2300/418* (2013.01)

(58) Field of Classification Search
None
See application file for complete search history.

(56) References Cited

U.S. PATENT DOCUMENTS

| 6,165,509 A | 12/2000 | Hoffman et al. |
| 6,348,558 B1 | 2/2002 | Harris et al. |

(Continued)

FOREIGN PATENT DOCUMENTS

| CN | 102458490 A | 5/2012 |
| CN | 103705985 B | 1/2016 |

(Continued)

OTHER PUBLICATIONS

Cote, D. et al., "Triamcinolone-Impregnated Nasal Dressing Following Endocsopic Sinus Surgery: A Randomized, Double-Blind, Placebo-Controlled Study", The Laryngoscope, vol. 120, No. 6, pp. 1269-1273.

(Continued)

*Primary Examiner* — Isis A Ghali
(74) *Attorney, Agent, or Firm* — Howard & Howard Attorneys PLLC (57) ABSTRACT

The present disclosure provides a foam nasal dressing for topically administering an active agent to a nasal cavity and for absorbing fluid discharge. The foam nasal dressing comprises a foamed core portion and a foamed shell portion arranged such that the foamed core portion is at least partially disposed within the foamed shell portion. The foamed shell portion has a porosity of greater than 80% and comprises a first phase-separated polymer and an active agent. The foamed core portion comprises a second phase-separated polymer with the first and second phase-separated polymers being the same or different. The present disclosure also provides a method of forming the foam nasal dressing.

13 Claims, 6 Drawing Sheets

(56) References Cited

U.S. PATENT DOCUMENTS

| | | |
|---|---|---|
| 6,355,699 B1 | 3/2002 | Vyakarnam et al. |
| 6,617,014 B1 | 9/2003 | Thomson |
| 6,784,273 B1 | 8/2004 | Spaans et al. |
| 6,835,336 B2 | 12/2004 | Watt |
| 7,780,980 B2 | 8/2010 | Sawhney |
| 7,858,078 B2 | 12/2010 | Hadba et al. |
| 7,951,131 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 8,357,361 B2 | 1/2013 | Hadba et al. |
| 8,481,651 B2 | 7/2013 | Hissink et al. |
| 8,663,686 B2 | 3/2014 | Zhang et al. |
| 8,740,929 B2 | 6/2014 | Gopferich et al. |
| 9,028,857 B2 | 5/2015 | Le Visage et al. |
| 9,084,876 B2 | 7/2015 | Makower et al. |
| 9,375,505 B2 | 6/2016 | Hedrich et al. |
| 9,422,389 B2 | 8/2016 | Chandrashekhar-Bhat et al. |
| 9,433,636 B2 | 9/2016 | Tijsma et al. |
| 9,592,299 B2 | 3/2017 | Sershen et al. |
| 9,610,377 B2 | 4/2017 | Hissink et al. |
| 9,662,400 B2 | 5/2017 | Smith et al. |
| 10,363,690 B2 | 7/2019 | Ladet et al. |
| 10,517,986 B2 | 12/2019 | Sherman et al. |
| 10,653,619 B2 | 5/2020 | Walsh |
| 2010/0221304 A1 | 9/2010 | Tan et al. |
| 2012/0114592 A1 | 5/2012 | Zuidema et al. |
| 2014/0329902 A1* | 11/2014 | Benns .............. A61M 31/002 514/564 |
| 2014/0336147 A1 | 11/2014 | Berman et al. |
| 2015/0320901 A1 | 11/2015 | Chandrashekhar-Bhat et al. |
| 2017/0014337 A1 | 1/2017 | Walsh |
| 2018/0028725 A1 | 2/2018 | Tooren et al. |
| 2018/0154003 A1 | 6/2018 | Sershen et al. |

FOREIGN PATENT DOCUMENTS

| | | |
|---|---|---|
| EP | 0605974 A1 | 7/1994 |
| EP | 1709103 B1 | 7/2016 |
| JP | 2015504867 A | 2/2015 |
| KR | 20160083779 A | 7/2016 |
| WO | 9901498 A1 | 1/1999 |
| WO | 9964491 A1 | 12/1999 |
| WO | 2004062704 A1 | 7/2004 |
| WO | 2016137327 A1 | 9/2016 |

OTHER PUBLICATIONS

English language abstract and machine-assisted English translation for CN 103705985 extracted from espacenet.com database on Jul. 16, 2020, 10 pages.

English language abstract and machine-assisted English translation for KR 20160083779 extracted from espacenet.com database on Jul. 16, 2020, 18 pages.

International Search Report for Application No. PCT/IB2018/060463 dated Apr. 3, 2018, 3 pages.

Solari, D. et al., "Endoscopic Anatomy of the Skull Base Explored Through the Nose", World Neurosurgery, vol. 82, No. 6, Supplement, 2014, pp. S164-S170.

Abstract of Stammberger, H. et al., "Functional Endoscopic Sinus Surgery", European Archives of Oto-Rhino-Laryngology, vol. 247, No. 2, 1990, pp. 63-76, 10 pages.

English language abstract for CN 102458490 A extracted from espacenet.com database on Dec. 28, 2021, 1 page.

English language abstract for JP 2015-504867 A extracted from espacenet.com database on Jan. 12, 2023, 2 pages.

* cited by examiner

BIOMEDICAL FOAM

CROSS-REFERENCE TO RELATED APPLICATION

This application is the National Stage of International Patent Application No. PCT/IB2018/060463, filed on Dec. 20, 2018, which claims the benefit of U.S. Provisional Patent Application No. 62/608,256, filed on Dec. 20, 2017, which are hereby incorporated by reference in their entirety.

TECHNICAL FIELD

The subject disclosure relates to a biomedical foam article (e.g. a foam nasal dressing) and a method of forming the biomedical foam article.

SUMMARY

An exemplary foam nasal dressing for topically administering a drug to a nasal cavity and for absorbing fluid discharge is provided. The foam nasal dressing comprises a foamed core portion, and a foamed shell portion arranged such that the foamed core portion is at least partially disposed within the foamed shell portion. The foamed core portion comprises a first polyurethane and includes amorphous segments and crystalline segments as well as a hemostatic agent. The foamed shell portion has a porosity of greater than 80%, comprises a second polyurethane, and includes amorphous segments and crystalline segments as well as a drug. In this example, the first and second polyurethanes can be the same or different. The nasal dressing has an elongate shape extending from a first end to a second end. A first half is adjacent the first end and a second half is adjacent the second end, wherein a weight of the drug in the first half of the foam nasal dressing is greater than a weight of the drug in the second half of the foam nasal dressing.

In another example, the foam nasal dressing for topically administering a drug to a nasal cavity and for absorbing fluid discharge is elongate and comprises a first foam and a second foam. The first foam has a porosity of greater than 80% and comprises a foamed base portion at a first end of the foam nasal dressing and a foamed core portion extending from the foamed base portion towards a second end of the foam nasal dressing. The foamed core portion comprises a first phase-separated polymer comprising amorphous segments and crystalline segments. The second foam has a porosity of at least 80% and comprises a foamed shell portion extending from the foamed base portion to the second end. The foamed shell portion comprises a second phase-separated polymer comprising amorphous segments and crystalline segments. In this example, the first and second phase-separated polymers are the same or different. The foamed base portion and the foamed shell portion cooperate to encapsulate the foamed core portion and define an outer surface of the nasal dressing. The foam nasal dressing of this example comprises the drug in a volume defining the second end and does not comprise the drug in a volume defining the first end.

In yet another example, the foam nasal dressing for topically administering a drug to a nasal cavity and for absorbing fluid discharge comprises a first foam and a second foam. The first foam has a porosity of greater than 80% and comprises a foamed base portion at a first end of the nasal dressing and a foamed core portion extending from the foamed base portion towards a second end of the nasal dressing. The foamed core portion comprises a first phase-separated polymer and a chitosan hemostatic agent. The second foam has a porosity of at least 80% and comprises a foamed shell portion extending from the foamed base portion to the second end. The foamed shell portion comprises a second phase-separated polymer and a drug. In this example, the first and second phase-separated polymers are the same or different. The foamed base portion and the foamed shell portion cooperate to encapsulate the foamed core portion and define an outer surface of the nasal dressing. The foam nasal dressing comprises the drug in a volume defining the second end and does not comprise the drug in a volume defining the first end. Further, the foam nasal dressing comprises the chitosan hemostatic agent in a volume defining the first end and does not comprise the chitosan hemostatic agent in a volume defining the second end.

A method of forming the foam nasal dressing for topically administering a drug to a nasal cavity and for absorbing fluid discharge is also provided. The method comprises providing a mold. The method also comprises placing a spacer and a first liquid in the mold, such that the first liquid and spacer are in contact in the mold. The first liquid comprises the first polyurethane and the drug. The method further comprises cooling the first liquid to freeze the first liquid and removing the spacer from the frozen first liquid to expose a cavity in the frozen first liquid. The method further comprises placing a second liquid in the cavity of the frozen first liquid. The second liquid comprises the second polyurethane that is the same as or different than the first polyurethane. The method further comprises cooling the second liquid to freeze the second liquid. The method further comprises drying the first and second frozen liquids to form the foam nasal dressing comprising the foamed core portion at least partially disposed within the foamed shell portion.

A method of simultaneously treating inflammation and absorbing fluid discharge from the sinus cavity with the foam nasal dressing is also disclosed. The method comprises the steps of providing the foam nasal dressing, compressing the foam nasal dressing such that the foam dressing assumes an insertion configuration, and positioning the foam nasal dressing within the nasal cavity while the foam nasal dressing is in the insertion configuration such that the second end of the foam nasal dressing is farther from the user than the first end.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION

In one example, a biomedical foam is a foam nasal dressing for topically administering an active agent to a nasal cavity and for absorbing fluid discharge. As shown in FIGS. 1-6, the foam nasal dressing 10 comprises a foamed core portion 12 and a foamed shell portion 14. The foamed shell portion 14 is arranged such that the foamed core portion 12 is at least partially disposed within the foamed shell portion 14.

Within the context of this disclosure "at least partially disposed within" requires that some volume of the foamed core portion 12 is disposed within a cavity of the foamed shell portion 14. In certain examples, from 10 to 100%, from 20 to 100%, from 30 to 100%, from 40 to 100%, from 50 to 100%, from 60 to 100%, from 70 to 100%, from 80 to 100%, or from 90 to 100%, of the total volume of the foamed core portion 12 is disposed within the foamed shell portion 14. In certain examples, the foamed shell portion 14 and foamed core portion 12 are not merely adjacent laminar layers. In yet another example, at least 50, 60, 70, 80, or 90% of the surface area of the foamed core portion 12 is covered by the foamed shell portion 14.

Of course, the foamed core portion 12 may be completely disposed within a cavity of the foamed shell portion 14, i.e. 100% of the total volume of the foamed core portion 12 is disposed within the foamed shell portion 14.

In many examples, the foam nasal dressing 10 is free from any lumen. That is, the foam nasal dressing 10 is substantially free of larger voids (aside from the relatively fine voids/cell structures of the foams that form the foam nasal dressing 10).

Referring now to the example of FIGS. 1-6, the foam nasal dressing 10 of this example has an elongate shape extending from a distal or a first end 16 to a proximate or a second end 18. Further, the foam nasal dressing 10 has a first half adjacent the first end 16 and a second half adjacent the second end 18. As shown in FIGS. 1-6, the first end 16 is furthest from the surgeon and the second end 18 is closest to the surgeon. In other words, when the foam nasal dressing 10 is inserted into a nasal cavity, the first end 16 is the first end to enter the nasal cavity and the second end 18 is relatively closer to the surgeon. In certain examples, as best shown in FIGS. 1A-C, 5, and 6, the foam nasal dressing 10 further comprises a foamed base portion 20 at the second end 18, with the foamed shell portion 14 and the foamed core portion 12 extending from the foamed base portion 20 towards the first end 16. When arranged in this manner, the foamed base portion 20 and foamed shell portion 14 may cooperate to encapsulate the foamed core portion 12 and define an outer surface of the foam nasal dressing 10. When the foamed shell portion 14 and the foamed base portion 20 cooperate to encapsulate the foamed core portion 12, the foamed core portion 12 is partially disposed within the foamed shell portion 14. In certain examples, such as shown in FIGS. 1A-C, 5, and 6, the foamed core portion 12 is entirely disposed within the foamed shell portion 14 and encapsulated due to the cooperation of the foamed shell portion 14 and foamed base portion 20. That is, the foamed core portion 12 may be completely disposed within a cavity formed by the foamed shell portion 14 and the foamed base portion 20, i.e. 100% of the total volume of the foamed core portion 12 is disposed within the foamed shell portion 14.

Referring back to the foamed shell portion 14, the foamed shell portion 14 is a foam having a porosity of greater than 80%. Alternatively, the foamed shell portion 14 has a porosity from 80 to 99%, from 80 to 96%, from 80 to 93%, from 80 to 90%, from 80 to 87%, from 80 to 84%, from 83 to 99%, from 85 to 99%, from 89 to 99%, from 92 to 99%, from 95 to 99%, from 83 to 96%, from 86 to 93%, from 92-98%, from 95-98%, or 90%. Porosity as referenced herein refers to a measure of the void (i.e. "empty") spaces in the foam, and is a fraction of the volume of pores/voids over the total volume, between 0 and 1, or as a percentage between 0% and 100%.

The foamed shell portion 14 comprises a first phase-separated polymer and an active agent. The first phase-separated polymer and the active agent are described in detail below. In certain examples, the foamed shell portion 14 of the foam nasal dressing 10 is the only portion of the foam nasal dressing 10 that includes an active agent. The geometric configuration of the foamed shell portion 14 is not particularly limited. In certain examples, a cross-section of the foamed shell portion 14 taken at a midpoint (i.e., half the distance between the first end 16 and second end 18 of the foam nasal dressing 10) may have a generally square or rectangular shape with a hollow interior. In these examples, the hollow interior is shaped to match the geometric configuration of the foamed core portion 12. Moreover, the exterior of the foamed shell portion 14 may be shaped as a cube or rectangular cuboid. In other examples, the exterior of the foamed shell portion 14 may have a generally cylindrical shape such that a cross-section taken at the midpoint of the foam nasal dressing 10 has a generally circular or oval shape with a hollow interior. In addition, as shown throughout FIGS. 1-6, the foamed shell portion 14 may include rounded corners about the first end 16 of the foam nasal dressing 10 to facilitate the insertion of the foam nasal dressing 10 into the nasal cavity of the patient. Alternatively, the foamed shell portion 14 may have a generally semi-spherical shape about the first end 16 of the foam nasal dressing 10 to facilitate insertion.

Figure 1A:
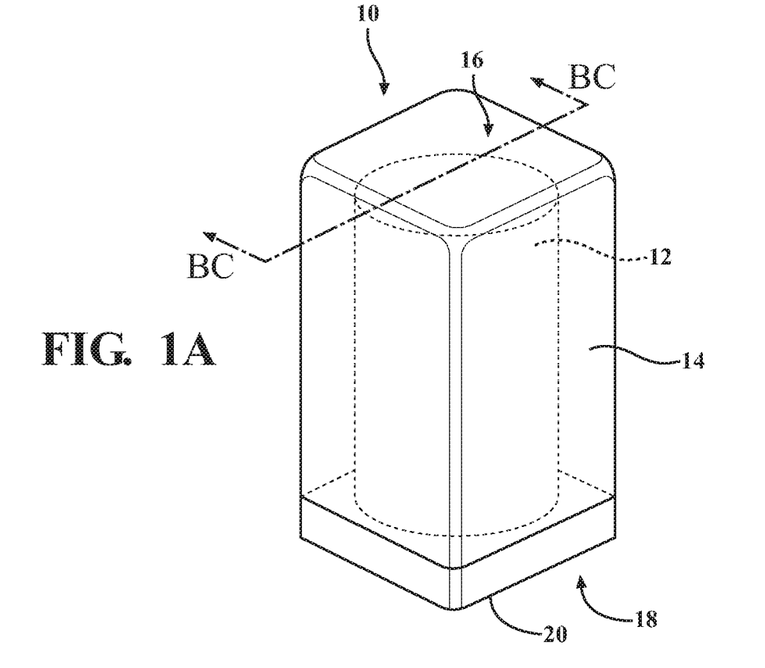
FIG. 1A is a perspective view of an example of the foam nasal dressing.
Figure 1B:
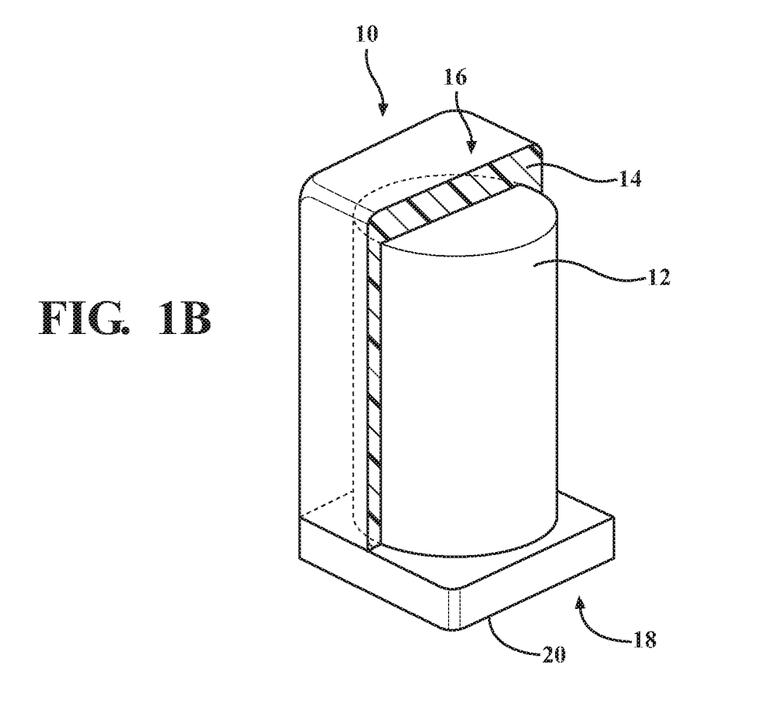
FIG. 1B is a perspective view of the example of FIG. 1A along line BC with a foamed shell portion shown in cross-section.
Figures 1C, 2, 3:
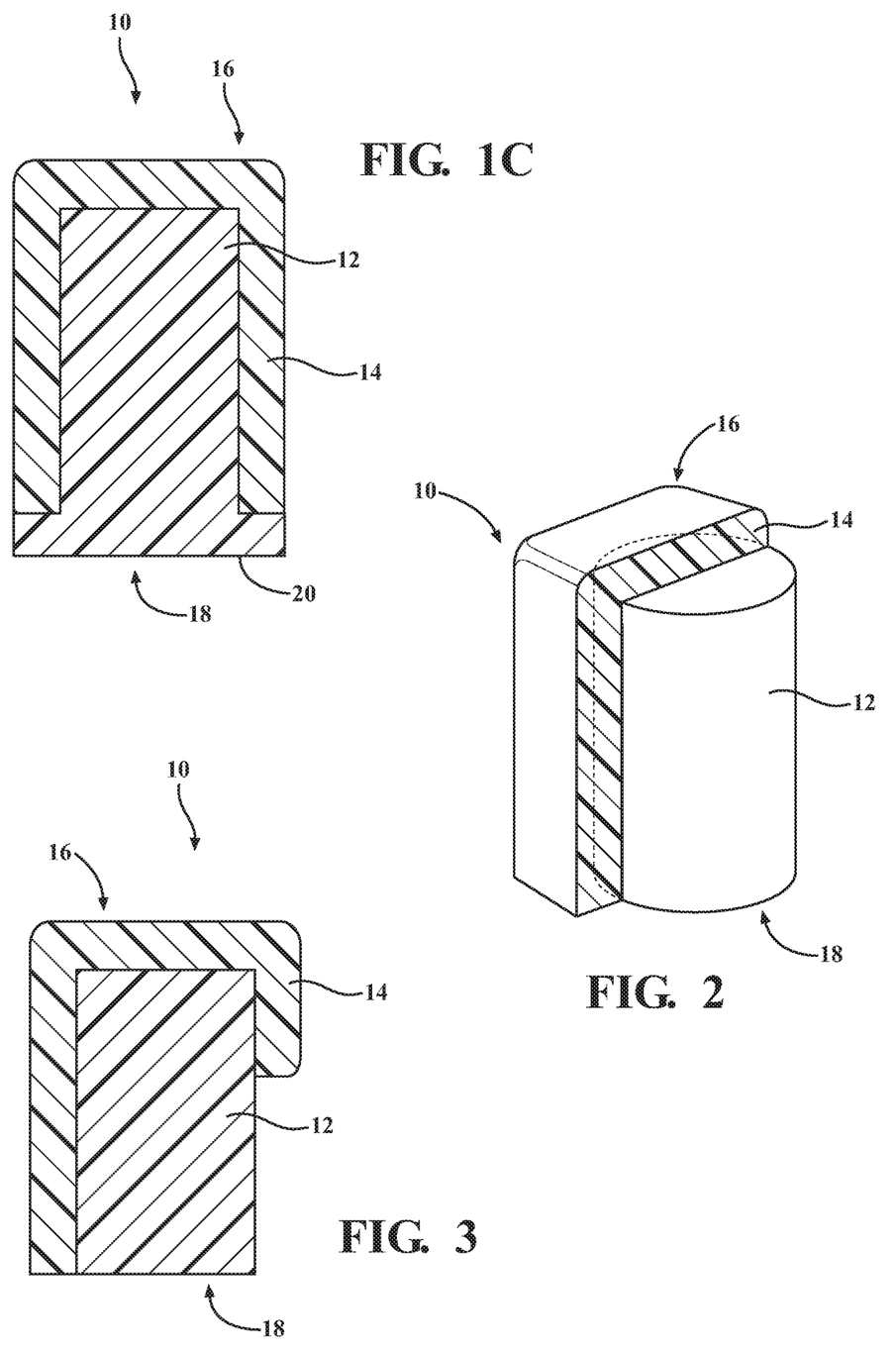
FIG. 1C is a cross-sectional view of the example of FIGS. 1A and 1B along line BC.
FIG. 2 is a top left perspective view of an example of the foam nasal dressing with a foamed shell portion shown in cross-section.
FIG. 3 is a cross-sectional view of another example of the foam nasal dressing.
Figure 4:
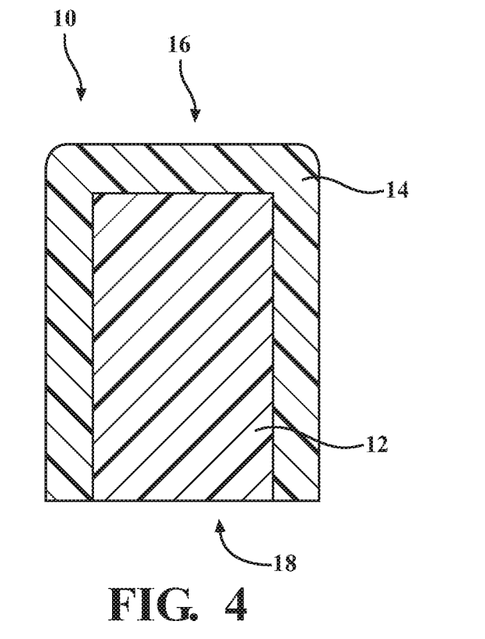
FIG. 4 is a cross-sectional view of another example of the foam nasal dressing.
Figure 5:
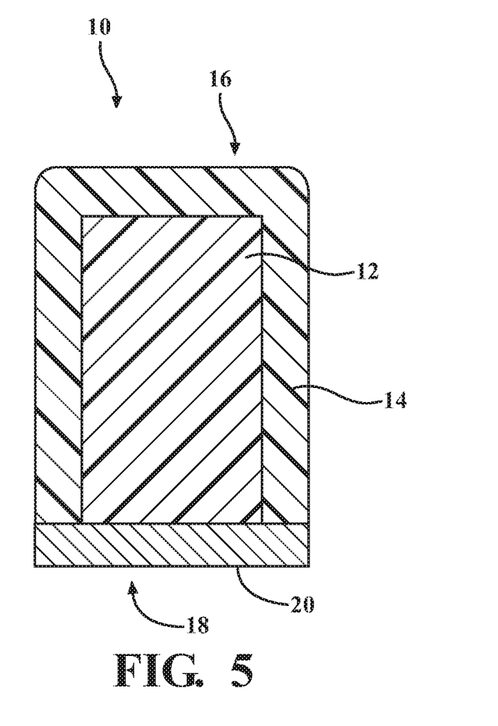
FIG. 5 is a cross-sectional view of another example of the foam nasal dressing.

As best shown in FIGS. 1A-C, the geometric shape of the foamed shell portion 14 reduces the error associated with the placement of the foam nasal dressing 10 in the nasal cavity of the patient. This is because a foam dressing should be placed in the nasal cavity in a manner in which the surface containing an active agent initially contacts a wound. Because the foam nasal dressing 10 of FIGS. 1A-C includes the foamed shell portion 14 as the predominant exterior surface, the surgeon can easily place the foam nasal dressing 10 in a nasal cavity and be confident that the foamed shell portion 14 (i.e., the active agent containing portion) will initially contact the wound, even when it is difficult for the surgeon to see the actual wound. In particular, the foamed shell portion 14 is the predominant exterior surface when it defines greater than 60, 70, 80, or 90% of the total exterior surface of the foam nasal dressing 10. In these examples, the foamed base portion 20 typically defines the remaining surface area. Accordingly, a relative amount of error is reduced when a relatively greater amount of the foamed core portion 12 is disposed within the foamed shell portion 14. This is true even when the foamed base portion 20 is included in the foam nasal dressing 10, because the first end 16 of the foam nasal dressing 10 is first inserted into the nasal cavity and the foamed base portion 20 is not located at the first end 16. Instead, the foamed base portion 20 is located at the second end 18, which is the end closest to the surgeon and less likely to contact the wound.

In certain examples, such as those shown in FIGS. 1A-C, 5, and 6, when the 100% of the foamed core portion 12 is disposed within the foamed shell portion 14, the foamed shell portion 14 is the predominant exterior surface (e.g. greater than 80%) of the foam nasal dressing 10, and it is near impossible for a surgeon to orient the foam nasal dressing 10 in a nasal cavity without the foamed shell portion 14 initially contacting the wound.

Of course, it is also possible to reduce surgeon error when less than 100% of the foamed core portion 12 is disposed within the foamed shell portion 14, such as shown in FIGS. 2 and 3. In FIG. 2, a perspective view of one example of the foam nasal dressing 10 with the foamed shell portion 14 shown in cross-section is illustrated. In the example foam nasal dressing 10 of FIG. 2, the foamed core portion 12 is partially disposed within the foamed shell portion 14. In FIG. 3, a cross-sectional view of another example of the foam nasal dressing 10 with the foamed core portion 12 partially disposed within the foamed shell portion 14 is illustrated.

Although the relative volume of the foamed shell portion 14 may vary depending on the particular application of the foam nasal dressing 10, in certain examples, the volume of the foamed shell portion 14 is from 20 to 40% based on a total volume of the foam nasal dressing 10. Alternatively, the volume of the foamed shell portion 14 is from 0.5 to 70%, from 1 to 60%, from 5 to 50%, from 10 to 50%, or from 15 to 45%, based on the total volume of the foam nasal dressing 10.

Referring now to the foamed core portion 12, the foamed core portion 12 comprises a second phase-separated polymer, which is the same as or different than the first phase-separated polymer. Although not required, the foamed core portion 12 may be active agent free (i.e., not including an active agent). In other words, in certain examples, the foamed core portion 12 does not include an active agent. In examples where the foamed core portion 12 includes an active agent, the active agent may be the same as or different than the active agent included in the foamed shell portion 14.

The foamed core portion 12 may have a porosity similar to the porosity of the foamed shell portion 14. For example, in certain examples, the foamed core portion 12 is a foam having a porosity of greater than 80%. Alternatively, the foamed core portion 12 may have a porosity from 80 to 99%, from 80 to 96%, from 80 to 93%, from 80 to 90%, from 80 to 87%, from 80 to 84%, from 83 to 99%, from 85 to 99%, from 89 to 99%, from 92 to 99%, from 95 to 99%, from 83 to 96%, from 86 to 93%, from 92-98%, from 95-98%, or 90%.

In examples where the foamed core portion 12 does not include an active agent, the foamed shell portion 14 may be the only portion of the foam nasal dressing 10 that includes an active agent. This particular design may be advantageous because it locates the active agent in the portion of the foam nasal dressing 10 (i.e., the foamed shell portion 14) that initially contacts the wound of the patient. In addition, it lowers the overall cost of the foam nasal dressing 10 by avoiding the inclusion of an active agent in portions that will not initially contact the wound. Finally, by optimizing the volume of the foamed shell portion 14 relative to the foam nasal dressing 10 as discussed above, the foam nasal dressing 10 may be designed to have excellent fluid absorption and mechanical properties with cost effective and efficient drug delivery. For example, the foam nasal dressing 10 may include an active agent free, foamed core portion 12 that is at least partially disposed within the foamed shell portion 14 with the foamed shell portion 14 being 20 to 40% of a total volume of the foam nasal dressing 10. Thus, not only does this example reduce the error associated with the placement of the foam nasal dressing 10 against a wound, it also optimizes the cost effectiveness of the active agent delivery.

The geometric configuration of the foamed core portion 12 is not particularly limited. In certain examples, such as shown in FIGS. 1-6, the foamed core portion 12 is cylindrically shaped. In other examples, a cross-section of the foamed core portion 12 taken at the midpoint of the foam nasal dressing 10 has a generally square or rectangular shape. In addition, similar to the foamed shell portion 14, the foamed core portion 12 may also include rounded corners or have a semi-spherical shape about the first end 16 of the foam nasal dressing 10.

Referring now to the foamed base portion 20, if included, the foamed base portion 20 typically has a porosity similar to the foamed shell portion 14 and foamed core portion 12. For example, the foamed base portion 20 typically has a porosity greater than 80%. Alternatively, the foamed base portion 20 may have a porosity from 80 to 99%, from 80 to 96%, from 80 to 93%, from 80 to 90%, from 80 to 87%, from 80 to 84%, from 83 to 99%, from 85 to 99%, from 89 to 99%, from 92 to 99%, from 95 to 99%, from 83 to 96%, from 86 to 93%, from 92-98%, from 95-98%, or 90%.

Figure 6:
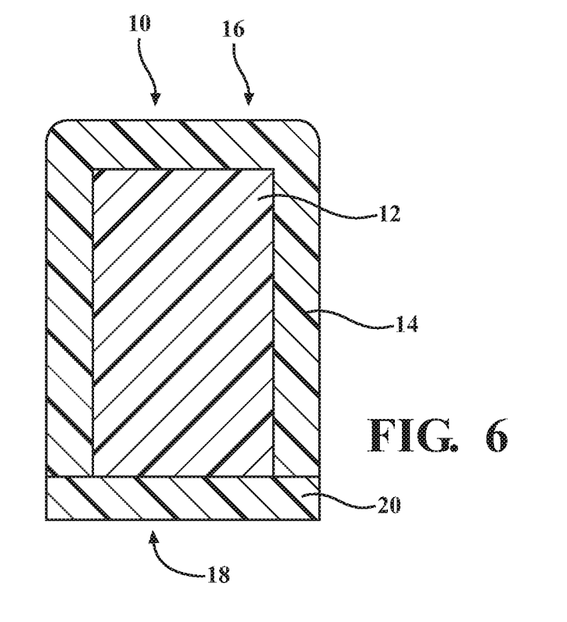
FIG. 6 is a cross-sectional view of another example of the foam nasal dressing.

The foamed base portion 20 may comprise a third phase-separated polymer with the third phase-separated polymer being the same as or different than either the first or second phase-separated polymers. The foamed base portion 20 may also include the active agent or may be free of an active agent. In certain examples, such as shown in FIG. 1C, the foamed base portion 20 and foamed core portion 12 are integral such that the chemical composition of the foamed base portion 20 is the same as the foamed core portion 12. In other examples, such as shown in FIG. 6, the chemical composition of the foamed base portion 20 is the same as the chemical composition of the foamed shell portion 14. In still further examples, such as show in FIG. 5, the chemical composition of the foamed base portion 20 is different than both the foamed core portion 12 and foamed shell portion 14.

The geometric configuration of the foamed base portion 20 is not particularly limited. In certain examples, a cross-section of the foamed base portion 20 is the same as the cross-section of the foamed shell portion 14 described above, with the exception that the cross-section of the foamed base portion 20 does not include a hollow interior. For example, in certain examples, both the cross-section of the foamed base portion 20 and foamed shell portion 14 are generally square or rectangular shaped. In these examples, the foamed core portion 12 is typically cylindrically shaped and is integral with the foamed base portion 20, such that the foamed core portion 12 and foamed base portion 20 are the same foam. For example, as best shown in FIG. 1C, the foamed base portion 20 and the foamed core portion 12 are integral and have the same chemical composition and porosity.

In examples with the foamed base portion 20 being drug free, the active agent loading in the foam nasal dressing 10 is not consistent throughout the foam nasal dressing 10. In particular, if the foam nasal dressing 10 was split in half based on volume, the weight of the active agent in the upper half (i.e., the half including the first end 16) is greater than the weight of the active agent in the lower half (i.e., the half including the second end 18). In other examples, if the foam nasal dressing 10 were to be divided into quarters based on volume, the weight of the active agent in the upper quarter (i.e., the weight of the active agent in the quarter containing the first end 16) would be greater than any other quarter. In addition, the weight of the active agent in the lower quarter (i.e., the quarter including the second end 18) would be less than any other quarter.

The foamed shell portion 14, foamed core portion 12, and/or the foamed base portion 20 may each individually have a foam density of 0.01 to 1.0 g/cm3. Alternatively, the foam density may be from 0.01 to 0.5, 0.01 to 0.3, 0.01 to 0.1, 0.01 to 0.09, 0.01 to 0.08, 0.01 to 0.07, 0.01 to 0.06, 0.01 to 0.05, 0.01 to 0.04, 0.01 to 0.03, 0.02 to 0.08, 0.04 to 0.08, 0.05 to 0.08, 0.06 to 0.08, 0.02 to 0.08, or 0.03-0.07 g/cm$^3$. In certain examples, the foamed shell portion 14, foamed core portion 12, and/or the foamed base portion 20 each have a porosity of 85-99% and a foam density of 0.03-0.07 g/cm3. It is to be appreciated that the term "foam density" as used throughout this disclosure refers to the density of foam, calculated as the phase-separated polymer mass per volume unit of a particular foam portion. Accordingly, if the particular foamed portion includes an active agent (e.g. the foamed shell portion 14 and optionally the foamed core portion 12 and foamed base portion 20), the mass of the active agent present in the particular foamed portion is disregarded when calculating the foam density.

Referring now to the first, second, and third phase-separated polymers, the term "phase-separated polymer" as used herein, refers to a polymer comprising soft (amorphous) segments, as well as hard (crystalline) segments, the hard segment having a phase transition temperature of at least mammalian body temperatures (which is generally 37° C. for humans) and the phase-separated morphology being manifest when the foam prepared from such a polymer is applied in the human or animal body for a sufficient period of time. Also, the polymer placed under temperature conditions comparable to the human or animal body exhibits the phase-separated morphology. A phase-separated polymer is characterized by the presence of at least two immiscible or partly miscible phases with a different morphology at normal environmental conditions. Within one material, a rubber phase and a crystalline phase (at a temperature above the glass transition temperature of the amorphous phase and below the melting temperature of the crystalline phase) may be present or a glassy and a crystalline phase (at a temperature below the glass transition temperature of the amorphous phase). Also at least two amorphous phases can be present at a temperature between the two phase transitions e.g. one glassy and one rubbery phase. At a temperature above the highest phase transition which is either a melting or glass transition temperature, the liquid and rubbery or the two rubbery phases, respectively, can form a phase mixed morphology or they can still be immiscible. Immiscible liquid and/or rubbery phases usually results in a polymer with a phase-separated morphology without the initial desired mechanical properties at normal environmental conditions.

The first, second, and third phase-separated polymers may each independently be selected from the group consisting of polyesters, polyethers, polyhydroxyacids, polylactones, polyetheresters, polycarbonates, polydioxanes, polyanhydrides, polyurethanes, polyester(ether)urethanes, polyurethane urea, polyamides, polyesteramides, poly-orthoesters, polyaminoacids, polyphosphonates, polyphosphazenes and combinations thereof. Such polymers are described in WO-A-99/64491, which is incorporated by reference in its entirety.

Without being bound to any particular theory, it is believed that the first phase-separated polymer of the foamed shell portion 14 may interact with the second phase-separated polymer of the foamed core portion 12. In particular, it is believed the crystalline (hard) segment (as described in WO 2004/062704, which is incorporated by reference in its entirety) of the first phase-separated polymer may form hydrogen bonds with the crystalline (hard) segment of second phase-separated polymer.

In certain examples, at least the foamed shell portion 14 or the foamed core portion 12 is also absorbent. Typically, both the foamed shell portion 14 and foamed core portion 12 are absorbent. As described in WO-A-2004/062704 the presence of the hydrophilic segment increases the absorption capacities of the particular foam portion and may influence the rate of biodegradation.

The term "biodegradable" as used herein, refers to the ability of a polymer to be acted upon biochemically in general by living cells, organisms, or part of these systems, including hydrolysis, and to degrade and disintegrate into chemical or biochemical products.

The term "bioresorbable" as used herein, refers to the ability of being completely metabolized by the human or animal body.

The term "amorphous" as used herein, refers to segments present in the phase-separated polymer with at least one glass transition temperature below the temperature of the cavities of the human or animal body into which the foam is packed, and may also refer to a combination of an amorphous and crystalline segment which is completely amorphous when packed in the human or animal body. For example, PEG in a pre-polymer may be crystalline in pure form, but may be amorphous when comprised in the R segment of a polyurethane of the formula (I). Longer PEG segments may also be partly crystalline when comprised in the R segment of a polyurethane of the formula (I), but will become amorphous ("dissolves") when placed in contact with water. Therefore such longer PEG segments are part of the soft segment of the phase-separated polymer of the formulas (I), whereas the hard segment should remain crystalline in nature to provide sufficient support for a particular foamed portion in the wet and packed state for, at least, a certain period of time.

The term "crystalline" as used herein, refers to segments, present in the phase-separated, that are crystalline when packed in the human or animal body, i.e., that have a melting temperature above the temperature of the cavities of the human or animal body into which the foam nasal dressing 10 is packed.

A "hydrophilic segment" as used herein, refers to a segment comprising at least one, preferably at least two, more preferably at least three hydrophilic groups such as can be provided for instance by C—O—C, or ether, linkages. A hydrophilic segment may thus be provided by a polyether segment. A hydrophilic segment may also be provided by polypeptide, poly(vinyl alcohol), poly(vinylpyrrolidone) or poly(hydroxymethylmethacrylate). A hydrophilic segment is preferably derived from polyalkyleneglycol, such as polyethyleneglycol, polypropyleneglycol, or polybutyleneglycol. The preferred hydrophilic segment is a polyethyleneglycol (PEG) segment.

The term "segment" as used herein, refers to a polymeric structure of any length. In the art of polymer technology a long polymeric structure is often referred to as a block, whereas a short polymeric structure is often referred to as a segment. Both these conventional meanings are understood to be comprised in the term "segment" as used herein.

In one particular example of the present application, the polymer is of the formula:

—[R-Q1[—R'—Z1-[R"—Z2-R'—Z3]p—R"—Z4]q—R'-Q2]n-    (I)

wherein R is selected from one or more aliphatic polyesters, polyetheresters, polyethers, polyanhydrides and/or polycarbonates, and optionally at least one R comprises a hydrophilic segment, R' and R" are independently C2-C8 alkylene, optionally substituted with C1-C10 alkyl or C1-C10 alkyl groups substituted with halides or protected S, N, P or O moieties and/or comprising S, N, P or O in the alkylene chain, Z1-Z4 are independently amide, urea or urethane, Q1 and Q2 are independently urea, urethane, amide, carbonate, ester or anhydride, n is an integer from 5-500, p and q are independent 0 or 1, provided that when q is 0, R is at least one amorphous aliphatic polyester, polyether, polyanhydride and/or polycarbonate segment with optionally at least one crystalline polyether, polyester, polyetherester or polyanhydride segment.

The simplest form of the phase-separated polymer, as represented by formula I, is of the formula: —R-Q1-R'-Q2-, i.e. when q=0.

The amorphous segment is comprised in the —R— part of the polymer according to formula (I). In case q=1, the Q1[—R'—Z1-[R"—Z2-R'—Z3]p-R"—Z4]q-R'-Q2 part of the polymer according to formula (I) represents the crystalline segment. In this particular case, the amorphous and crystalline segments are alternating, thus providing the hard segment with a uniform block-length.

As described above, R may represent a mixture of two or more different types of aliphatic polyesters, polyetheresters, polyethers, polyanhydrides and/or polycarbonates, which mixture comprises both amorphous and crystalline types, so that both are comprised in a particular foamed portion. In the case that a mixture of amorphous and crystalline types of R segments are provided in a polymer according to the formula (I), optionally at least one hydrophilic segment is provided in at least one amorphous R segment.

R may in particular be derived from the cyclic monomers lactide (L, D or LD), glycolide, ε-caprolactone, δ-valerolactone, trimethylenecarbonate, tetramethylenecarbonate, 1,5-dioxepane-2-one, para-dioxanone, and combinations thereof and optionally polyethyleneglycol, polypropyleneglycol, polybutyleneglycol and combinations thereof. In certain examples, R is an amorphous polyester derived from exclusively lactide and ε-caprolactone, with a molecular weight between 1000 and 4000. In one example, R is about 25 wt. % lactide, about 25 wt. % ε-caprolactone and about 50 wt. % of polyethyleneglycol.

In a phase-separated polymer according to the formula (I), Q1 and Q2 may be selected from amide, urea, urethane ester, carbonate or anhydride groups, whereas Z1 through Z4 should be chosen from amide, urea or urethane groups so that at least 4 hydrogen bond forming groups are present in a row in the crystalline segment. The group R' in —Z2-R'—Z3- may be different or similar to R' in -Q1-R'—Z1- or —Z4-R'-Q2-.

As stated, R optionally comprises a hydrophilic segment and such a hydrophilic segment can very suitably be an ether segment, such as a polyether segment derivable from such polyether compounds as polyethyleneglycol, polypropyleneglycol or polybutyleneglycol. Also, a hydrophilic segment comprised in R may be derived from polypeptide, poly(vinyl alcohol), polyvinylpyrrolidone) or poly(hydroxymethylmethacrylate). A hydrophilic segment is preferably a polyether such as poly(ethylene glycol), poly(propylene glycol) or poly (butylene)glycol.

In certain examples, the amorphous segment comprises a hydrophilic segment. The hydrophilic segment may comprise polyethyleneglycol in an amount of 1-80 wt %, more preferably 5-60 wt %, even more preferably 20-50 wt %, most preferably 50 wt %, based on the total weight of the hydrophilic segment.

In certain examples, the phase-separated polymer is a polymer according to formula I, wherein R' is $(CH_2)_4$, R" is $(CH_2)_4$, or both R' and R" are $(CH_2)_4$. For example Z1-Z4 may be a urethane.

It should be appreciated that the foams described herein are comprised of a plurality of polymer chains, with each of the polymer chains comprising the phase-separated polymer, e.g. a polyurethane. In many examples, the foams are substantially free of any covalent cross-linking between polymer chains included in the foam. In the context of this disclosure, the term "substantially free of any covalent cross-linking" means that one polymer chain has less than 20, less than 10, less than 6, less than 4, or less than 2 covalent bonds to other polymer chains included in the foam. In some examples, the foam is free of any covalent cross-linking between polymer chains included in the foam. In other words, each polymer chain is not covalently cross-linked to any other polymer chain included in the foam.

In some preferred examples, the phase-separated polymer is a polyurethane foam including amorphous segments and crystalline segments, the crystalline segments formed via hydrogen bonding. In such examples, the crystalline segments may include the reaction product of 1,4 butanediol and 1,4 diisocyanatobutane, while the amorphous segments in the polyurethane foam may include a polyalkylene glycol, e.g. poly(ethylene glycol), a polyester, e.g. polyglycolide, or a combination of the two.

The term "hydrogen bonding" as used herein, refers to a partially electrostatic attraction between a hydrogen (H) atom which is bound to a more electronegative atom or group, such as nitrogen (N), oxygen (O), or fluorine (F)—the hydrogen bond donor—and another adjacent atom bearing a lone pair of electrons—the hydrogen bond acceptor. In polyurethanes, hydrogen bonding between carbonyl and N—H groups is one of the major driving forces for phase separation. Hydrogen bonds may be intermolecular (occurring between separate molecules) or intramolecular (occurring among parts of the same molecule).

In such examples, the foams described herein comprise hard/crystalline and soft/amorphous segments. The hard segments are formed via hydrogen bonding between urethane segments of each polymer chain. While not wishing to be bound by one particular theory, it is believed that urethane segments of each polymer chain are particularly susceptible to hydrogen bonding with other urethane segments in adjacent polymer chains. Accordingly, during formation of the foam, the urethane segments of each polymer chain are hydrogen bonded to, and thereby aligned with, the urethane segments of other polymer chains included in the foam. Because the urethane segments of each polymer chain are aligned with urethane segments of the other polymer chains, the polyetherester segments of each polymer chain are necessarily aligned with the polyetherester segments of other polymer chains included in the foam. The alignment of these polyetherester segments forms the soft segments of the foam. As such, because of the hydrogen bonding between urethane segments of each polymer chain, the foam exhibits a highly organized three-dimensional network structure of hard and soft segments.

Accordingly, the polyurethane foam of this preferred example includes crystalline segments formed via hydrogen bonding. Further, it is believed that the crystalline segments comprising the reaction product of 1,4 butanediol and 1,4 diisocyanatobutane and the amorphous segments comprising poly(ethylene glycol) form crystalline segments and the amorphous segments that "stack" in an alternating configuration to provide a 3-dimensional porous structure, which is strengthened via hydrogen bonding between the stacked crystalline segments.

Furthermore, the polyurethane foam of this preferred example readily interacts with other polymers (or portions) to hydrogen bond because it includes the crystalline segments comprising the reaction product of 1,4 butanediol and 1,4 diisocyanatobutane and the amorphous segments comprising poly(ethylene glycol).

In many examples, the various portions 12, 14, and 20 may include the phase-separated polymer comprising polyurethane foam including amorphous segments and crystalline segments, the crystalline segments formed via hydrogen bonding. In such examples, the crystalline segments may include the reaction product of 1,4 butanediol and 1,4 diisocyanatobutane, while the amorphous segments in the polyurethane foam include a polyalkylene glycol, e.g. poly (ethylene glycol). In such examples, the foamed shell portion 14, the foamed core portion 12, and the foamed base portion 20 (if included) are bonded to one another via hydrogen bonding and substantially free of covalent bonds therebetween. In such examples, the foam nasal dressing 10 exhibits excellent structural characteristics in dry conditions as well as in the presence of moisture.

The combination of the particular phase-separated polymer in each particular foam portion in addition to the porosity, pore size, and foam density establishes the physical properties of the particular foam portion. In particular, it is possible to achieve to good compressibility, which means that the foam retains its structure (in particular its compression strength) when having absorbed or being saturated with a liquid, such as blood. The mechanical, structural and chemical properties of the foam are mainly determined by the polymer present in the foam. This is advantageous, because it provides for a way to control and adjust the mechanical, structural and chemical properties by selecting a suitable phase-separated polymer.

The foamed shell portion 14, foamed core portion 12, and/or the foamed base portion 20 may each include the drug, be substantially free of the drug, or free of the drug. The term "substantially free" as used with reference to any of the active agents or drugs described herein may be defined as less than 5, 4, 3, 2, 1, 0.5, 0.1, 0.05, or 0.01 wt. %, based on a total weight of a particular portion or on a total weight of the foam nasal dressing 10. The disclosure that contemplates "substantially free of" as also encompasses "free of". As such, when the portions and/or foam nasal dressing 10 are described as "substantially free of" something, e.g. a drug, this descriptive language can be narrowed to "free of".

In one example, the foamed core portion 12 includes a first drug at a first concentration, and the foamed shell portion 14 includes a second drug, which is the same as or different than the drug, at a second concentration. For example, the foamed core portion 12 may include chitosan or a derivative thereof at a first concentration, and the foamed shell portion 14 may comprise a steroid such as mometasone furoate at a second, different concentration.

The drug included in each particular foam portion of the foam nasal dressing 10 is substantially located in the cell wall of the foam. This is in contrast to foams that include drugs predominately within the voids of the foam. Without wishing to be bound by theory, it is believed that when drugs are substantially located in the voids, drug release is non-controlled and about instantaneous. In contrast, when drugs are located within the cell walls of the pores, the porosity of the particular drug containing foamed portion influences the release rate of the active agent. The higher the porosity, the higher the rate of release and vice versa. Without wishing to be bound by theory, it is believed that an increased porosity results in an increased degradation rate of the particular foamed portion and thereby an increased release rate. In other words, the degradation of the particular foamed portion (e.g. the foamed shell portion 14) controls the release rather than an additive.

The rate of release of the active agent from the particular foamed portion of the foam nasal dressing 10 including the active agent may be expressed as the time required to release a certain amount of drug in a certain amount of time. Typically, 8 hours to 1.5 days are required to release 50% of the active agent from the foamed shell portion 14. In particular examples, it may be preferred that 50% of the active agent is released in a longer time, e.g. in 1 to 5 days. To release about 100% (e.g. more than 95%) of the active agent, a time of 4 to 14 days is generally preferred.

Typically, the active agent is a drug (i.e., any pharmaceutically active compound), an antibiotics, an anti-inflammatory agent, a, corticosteroid, a hemostatic agent, an anti-allergen, an anti-cholinergic agent, an antihistamine, an anti-infective, an anti-platelet, an anti-coagulant, an anti-thrombic agent, an anti-scarring agent, an anti-proliferative agent, a chemotherapeutic agent, an anti-neoplastic agent, a pro-healing agent, decongestant, a vitamin, a hyperosmolar agent, an immunomodulator, an immunosuppressive agent, or combinations thereof. In one example, the active agent is a steroidal anti-inflammatory agent. It has been found that the relatively slow release of the active agent from the foamed shell portion 14 is particularly suitable for steroidal anti-inflammatory agents, such as corticosteroids.

In some examples, the active agent is a molecule including at least one hydrogen atom, which is bound to a nitrogen, oxygen, or fluorine atom. This structure facilitates hydrogen bonding between the active agent and phase separated polymer, e.g. the polyurethane foam comprising the crystalline segments comprising the reaction product of 1,4 butanediol and 1,4 diisocyanatobutane and the amorphous segments comprising poly(ethylene glycol). In other words, the active agent may advantageously include hydrogen atoms that are available to form a hydrogen bond with the crystalline segments of the phase-separated polymer, e.g. polyurethane. Hydrogen bonding between the active agent and the phase-separated polymer may help control and slow down the release of the active agent.

In one example, the active agent is a steroidal anti-inflammatory agent. It has been found that the relatively slow release of the active agent from the phase-separated polymer is particularly suitable for steroidal anti-inflammatory agents, such as corticosteroids. In some examples, the foamed shell portion 14 includes the steroid, and the foamed core portion 12 is substantially free of the steroid. In such examples, the steroid may include least one hydrogen atom, which is bound to a nitrogen, oxygen, or fluorine atom, e.g.

the atom being available to form a hydrogen bond with the crystalline segments of the foamed shell portion 14.

In another example, the active agent is a hemostatic agent. Of course, the foam nasal dressing 10 may include both an anti-inflammatory agent, e.g. a steroid, and a hemostatic agent. In various examples, the hemostatic agent includes at least one hydrogen atom bonded to a nitrogen atom, and/or at least one hydrogen atom bonded to an oxygen atom, with the hydrogen atoms being available to form a hydrogen bond with the crystalline segments of the first and/or second polyurethane foam. In such examples, molecules of the hemostatic agent and molecules of the phase-separated polymer are bonded to one another via hydrogen bonding and substantially free of covalent bonds therebetween.

In certain examples, when the active agent is a hemostatic agent, it is believed that the interaction between the phase-separated polymer and the hemostatic agent in the foam nasal dressing 10 leads to a synergistic effect with respect to the hemostatic activity, particularly when using the phase-separated polymer and a chitosan hemostatic agent. The hemostatic agents including their synergistic effect with phase-separated polymers are described in U.S. Pat. App. Pub. 2015/0320901, which is incorporated by reference in its entirety.

In certain examples, the hemostatic agent is a chitosan hemostatic. The term "chitosan hemostatic agent" as used herein refers to chitosan or a salt or derivative thereof. Good results have been obtained using chitosan or chitosan acetate.

Chitosan is a polysaccharide comprising D-glucosamine units (deacetylated units) and N-acetyl-D-glucosamine units (acetylated units). Chitosan can be prepared from chitin by deacetylating at least part of the N-acetyl-D-glucosamine in chitin (poly-N-acetyl-D-glucosamine) by hydrolysis. The ratio of D-glucosamine units and N-acetyl-D-glucosamine units in chitosan is typically expressed as the degree of deacetylation. The degree of deacetylation is defined as the percentage of glucosamine units in chitosan that are not acetylated. This percentage thus corresponds to the molar percentage of deacetylated units present in chitosan. Without being bound by theory, it is believed that a higher degree of deacetylation improves the hemostatic properties. The chitosan may have a degree of deacetylation of 1-100 mol %, 25-100 mol %, 50-100 mol %, 75-100 mol %, 85-100 mol %, 90-100 mol %, 5-50 mol %, 10-35 mol %, or 10-25 mol %. The above values also apply to chitosan present in chitosan salts, as well as to chitosan derivatives (which have acetylated and deacetylated units just like chitosan itself). In additional non-limiting examples, all values and ranges of values within and including the aforementioned range endpoints are hereby expressly contemplated. Without being bound by theory, it is believed that a higher degree of deacetylation improves the hemostatic properties of the chitosan.

Suitable chitosan salts are those with the chitosan ion having a net positive charge. Accordingly, suitable chitosan salts may be salts consisting of a chitosan cation and a counter anion. For example, the chitosan hemostatic agent may be a salt of chitosan with an organic acid, in particular with a carboxylic acid such as succinic acid, lactic acid or glutamic acid. Chitosan salts may for example be selected from the group consisting of nitrate, phosphate, glutamate, lactate, citrate, acetate and hydrochloride salts of chitosan.

In general, a chitosan derivative is a chitosan molecule wherein one or more of the hydroxyl groups and/or the amine group present in chitosan has been substituted. For example, the one or more hydroxyl groups may be substituted to obtain an ether or ester. The amine group may be substituted to obtain an amino group, although this generally results in a decrease in hemostatic activity. Therefore, the amine groups of chitosan are typically unsubstituted.

The chitosan hemostatic agent may comprise or be derived from chitosan originating from animals, plants or shellfish. These sources give similar good results with respect to the hemostatic effects described above. Furthermore, synthetic chitosan may also be used.

Further examples of suitable chitosan salts are chitosan esters of glutamate, succinate, phtalate or lactate, chitosan derivatives comprising one or more carboxymethyl cellulose groups, carboxymethyl chitosan. Other suitable examples of chitosan derivates are chitosan with quaternary groups (like N-thrimethylene chloride, N-trimethylene ammonium). Also, bioactive excipients such as calcitonin or 5-methylpyrrolidinone can be used.

The chitosan hemostatic agent may have a molecular weight in the range of about 1-1000 kDa.

IN various examples, the chitosan hemostatic agent may have a molecular weight in a range of about 1-1000 kDa, 1-500 kDa, 1-250 kDa, 1-100 kDa, 10-1000 kDa, 10-500 kDa, 10-250 kDa, 10-100 kDa, 30-80 kDa, 50-1000 kDa, 50-500 kDa, 50-350 kDa, 50-250 kDa, 100-1000 kDa, 100-750 kDa, 100-500 kDa, 100-250 kDa 150-500 Kda, 200-1000 kDa, 200-750 kDa, 200-500 kDa, 225-275 kDa, 200-300 kDa, 210-390 kDa, 90-1000 kDa, 290-1000 kDa, 290-1000 kDa, or 390-1000 kDa. In additional non-limiting examples, all values and ranges of values within and including the aforementioned range endpoints are hereby expressly contemplated.

In one example, as best shown in FIGS. 1A-C, the foam nasal dressing 10 for topically administering an active agent to a nasal cavity and for absorbing fluid discharge, comprises a first foam having a porosity of greater than 80%. The first foam comprises a foamed base portion 20 at the second end 18 of the foam nasal dressing 10 and a foamed core portion 12 extending from the foamed base portion 20 towards a first end 16 of the foam nasal dressing 10. With the second end 18 being the closest to the surgeon and the first end 16 being furthest from the surgeon. The foam nasal dressing 10 further comprises a second foam having a porosity of at least 80%. The second foam comprises a foamed shell portion 14 extending from the foamed base portion 20 to the first end 16. The foamed shell portion 14 comprises a first phase-separated polymer and an active agent (e.g. a corticosteroid). The foamed base portion 20 and the foamed shell portion 14 cooperate to encapsulate the foamed core portion 12 and define an outer surface of the nasal dressing 10. The foamed shell portion 14 comprises a second phase-separated polymer, which is same as or different than the first phase-separated polymer. The foam nasal dressing 10 comprises the active agent (e.g. a steroid) at the first end 16 and does not comprise the active agent at the second end 18. Although not required, the first foam may also comprise the chitosan hemostatic agent. When the chitosan hemostatic agent is included in the first foam, the foam nasal dressing 10 may comprise the chitosan hemostatic agent at the second end 18 and may not comprise the chitosan hemostatic agent at the first end 16. In some examples, the chitosan hemostatic agent is homogenously distributed within the foamed core portion 12, and the drug, e.g. steroid, is homogenously distributed within the foamed shell portion 14.

In certain examples the foamed core portion 12 and the foamed base portion 20 are integral (i.e., the foamed base and shell portions 20, 14 are a unitary foam with the same chemical composition, porosity, etc.) and include a chitosan hemostatic agent as an active agent. In these examples, the foamed shell portion 14 may include a different active agent. Furthermore, the foamed shell portion 14 and foamed base portion 20 may cooperate to encapsulate the foamed core portion 12. When the foamed shell portion 14 includes a different active agent, the active agent is typically a corticosteroid. In these examples, the chitosan hemostatic agent is present at the second end 18 but absent at the first end 16 of the foam nasal dressing 10. Conversely, the corticosteroid is present at the first end 16 and absent at the second end 18 of the foam nasal dressing 10.

In certain examples, when the active agent is the hemostatic agent, the foamed portion including the hemostatic agent (i.e., the foamed shell portion 14 and/or the foamed core portion 20) has a porosity of 85-99% and a foam density of 0.03-0.07 g/cm3. Such values for the porosity and density contribute to the enhanced hemostatic activity and also provide the foam with good liquid (e.g. water or blood) absorbing properties. Alternatively, the foamed portion has a foam density of 0.03-0.07 g/cm3 and a porosity of 92-98% or 95-98%.

The amount of hemostatic agent may be at least 0.1 wt. %, preferably at least 2 wt. %, more preferably at least 5. wt. % of the total weight of the foam portion comprising the hemostatic agent. Notably, even this relatively small amounts of hemostatic agent is sufficient to provide the foam nasal dressing 10 with desirable hemostatic properties. Furthermore, the amount of hemostatic agent is generally less than 99 wt. %, less than 50 wt. %, or less than 35 wt. % of the total weight of the foam portion. Since the hemostatic activity of the foam nasal dressing 10 is almost independent on hemostatic agent, high concentrations are generally neither required nor preferred.

The hemostatic agent is preferably present in the foam in the form of particles, in particular polymeric particles. Examples of suitable particles are amorphous, crystalline and gel-like particles. The hemostatic agents may also be liquid, in particular when highly viscous. In case of hemostatic particles, the particles may have a size from 1-1000 μm. Preferably, particles are smaller than 150 μm. In particular good results have been obtained using particles of 5-90 μm. Small particles have a number of advantages. First, the structure of the foam is less influenced by the presence of small particles than large particles. Second, small hemostatic particles have a smaller tendency to aggregate than large particles. Furthermore, a good dispersion may be obtained using small particles. Lastly, small particles do not settle down when preparing the foam, such that a homogeneous distribution within the foam may be achieved if desirable.

The hemostatic particles may be any suitable shape but are preferably roughly spherical. The particles are preferably solid. Suitable solid particles to be used are generally insoluble and hydrophilic.

In some examples, the chitosan hemostatic agent is homogenously distributed within the foamed core portion 12, and the drug, e.g. the steroid, is homogenously distributed within the shell 14 portion. In other examples, the hemostatic agent is insoluble in the first separated polymer (e.g. first polyurethane foam) and the drug, e.g. steroid, is insoluble in the second phase-separated polymer (e.g. second polyurethane foam).

In a first, non-limiting example, the foam nasal dressing 10 for topically administering an active agent to a nasal cavity and for absorbing fluid discharge comprises the foamed core portion 12 and the foamed shell portion 14. The foamed shell portion 14 is arranged such that the foamed core portion 12 is at least partially disposed within the foamed shell portion 14. Further, the foamed shell portion 14 has a porosity of greater than 80% and comprises the first phase-separated polymer and the active agent. The foamed core portion 12 comprises a second phase-separated polymer. In this example, the first and second phase-separated polymers are the same or different.

In a second non-limiting example, the foam nasal dressing 10 for topically administering a drug to a nasal cavity and for absorbing fluid discharge comprises the foamed core portion 12 and the foamed shell portion 14. The foamed core portion 12 comprises a first polyurethane including amorphous segments and crystalline segments, the crystalline segments formed via hydrogen bonding. The foamed core portion 12 also comprises a hemostatic agent. The foamed shell portion 14 is arranged such that the foamed core portion 12 is at least partially disposed within the foamed shell portion 14. The foamed shell portion 14 has a porosity of greater than 80% and comprising a second polyurethane including amorphous segments and crystalline segments, the crystalline segments formed via hydrogen bonding. In this example, the first and second polyurethanes are the same or different. In this example, the active agent or drug, e.g. a steroid, is disposed in the foamed shell portion 14. Further, in this example, the foam nasal dressing 10 has an elongate shape extending from the first end 16 to the second end 18. The foam nasal dressing 10 has the first half adjacent the first end 16 and the second half adjacent the second end 18, wherein a weight of the drug in the first half of the foam nasal dressing 10 is greater than a weight of the drug in the second half of the foam nasal dressing 10.

In a third, non-limiting example, the foam nasal dressing 10 for topically administering a drug to a nasal cavity and for absorbing fluid discharge is elongate. In this example, the foam nasal dressing 10 comprises a first foam having a porosity of greater than 80%. The first foam comprises (or forms) the foamed base portion 20. The first foam is at the first end 16 of the foam nasal dressing 10 and the foamed core portion 12 extends from the foamed base portion 20 towards the second end 18 of the foam nasal dressing 10. The foamed core portion 12 comprises a first phase-separated polymer. The first phase-separated polymer comprises an amorphous segment and a crystalline segment. The foam nasal dressing 10 of this example includes a second foam having a porosity of at least 80%. The second foam comprises (or forms) the foamed shell portion 14, which extends from the foamed base portion 20 to the second end 18. The foamed shell portion 14 comprises a second phase-separated polymer and a drug, e.g. a steroid. The second phase-separated polymer comprises an amorphous segment and a crystalline segment. In this example, the foamed base portion 20 and the foamed shell portion 14 cooperate to encapsulate the foamed core portion 12 and define an outer surface of the foam nasal dressing 10. In this example, the first and second phase-separated polymers are the same or different. Further, the foam nasal dressing 10 comprises the drug in a volume defining the second end, and does not comprise the drug in a volume defining the first end.

In a fourth, non-limiting example, the foam nasal dressing 10 for topically administering a drug to a nasal cavity and for absorbing fluid discharge is elongate. In his example, the foam nasal dressing 10 comprises a first foam having a porosity of greater than 80%. The first foam comprises (or forms) the foamed base portion 20. The first foam is at the first end 16 of the foam nasal dressing 10 and the foamed core portion 12 extends from the foamed base portion 20 towards the second end 18 of the foam nasal dressing 10. The foamed core portion 12 comprises a first phase-separated polymer. The first phase-separated polymer comprises an amorphous segment and a crystalline segment. The foam nasal dressing 10 of this example includes a second foam having a porosity of at least 80%. The second foam comprises (or forms) the foamed shell portion 14, which extends from the foamed base portion 20 to the second end 18. The foamed shell portion 14 comprises a second phase-separated polymer and a drug. The second phase-separated polymer comprises an amorphous segment and a crystalline segment. In this example, the foamed base portion 20 and the foamed shell portion 14 cooperate to encapsulate the foamed core portion 12 and define an outer surface of the foam nasal dressing 10. In this example, the first and second phase-separated polymers are the same or different, typically different. In this example, the foam nasal dressing 10 may comprise the drug in a volume defining the first end 16, and does not comprise the drug in a volume defining the second end 18, and the foam nasal dressing 10 comprises a chitosan hemostatic agent in a volume defining the second end, and does not comprise the chitosan hemostatic agent in a volume defining the first end.

Without departing from the broadest scope of the disclosure, it is to be appreciated that the biomedical foam as described above relating to a foam nasal dressing 10 may also be used in other biomedical foam applications such as foams for ear dressings or for packing an atrium. When the biomedical foam is a foam ear dressing or packing an atrium, the foam includes the foamed shell portion 14, foamed core portion 12, and optionally the foamed base portion 20' as described above. Similarly, the foam is formed using the method for forming the foam nasal dressing 10. In other words, each and every example of this disclosure is applicable to the foam ear dressing and/or atrium packing.

Figure 7:
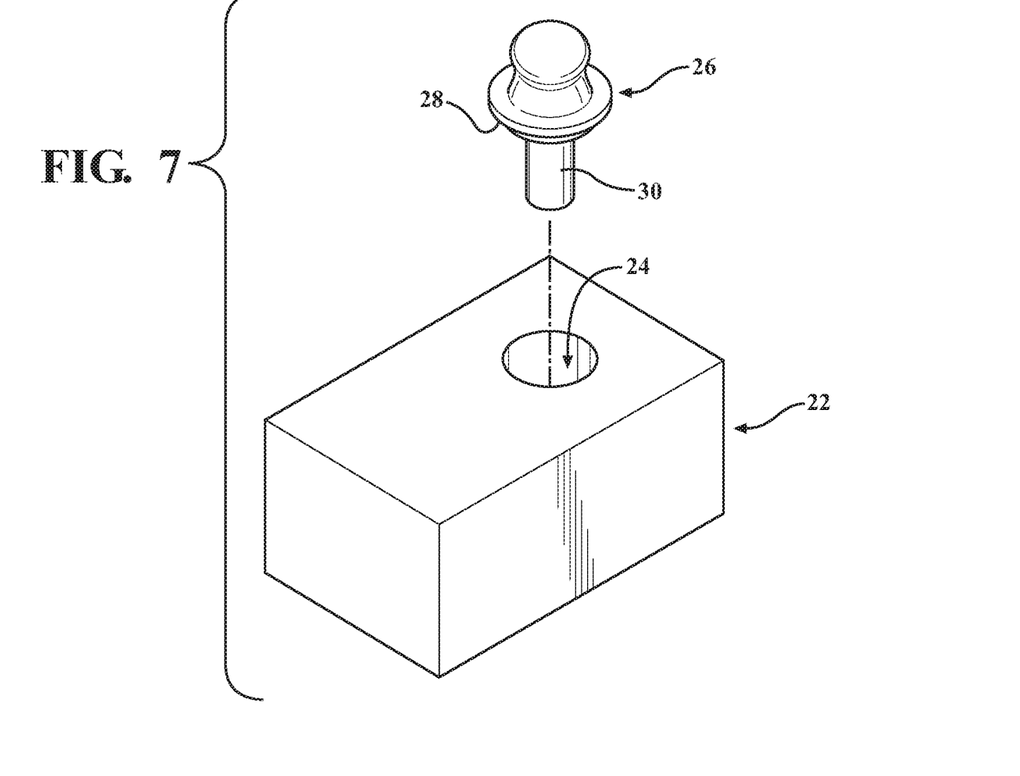
FIG. 7 is perspective view of a mold and a spacer.
Figure 8:
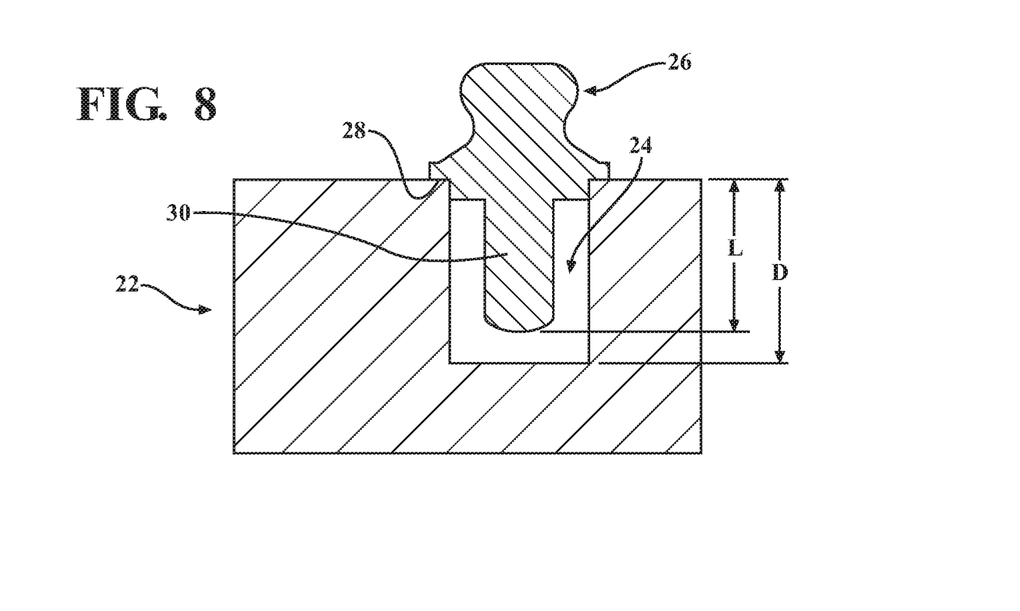
FIG. 8 is a cross-sectional view of the mold and the spacer of FIG. 7.

The present disclosure also provides a method of forming a foam nasal dressing 10. As shown in FIGS. 7 and 8, the method comprises providing a mold 22. The mold 22 may have a cavity 24 of any suitable shape and/or size. In the illustrated example, the cavity 22 is cylindrically-shaped.

As also shown in FIGS. 7 and 8, the method further comprises placing a spacer 26 in the mold 22. Although the shape of the spacer 26 is not particularly limited, the shape should prevent the spacer 26 from reaching the bottom of the cavity 24 of the mold 22. For example, as illustrated in FIGS. 7 and 8, the spacer 26 may include a lip 28 and a protrusion 30. Typically, the lip 28 will rest against an exterior surface of the mold 22 and prevent the spacer 26 from contacting the bottom of the cavity 24 of the mold 22. In other words, the lip 28 may cooperate with the exterior surface of the mold 22 to suspend the protrusion 30 in the cavity 24 of the mold 22. In these examples, a length (L) of the protrusion 30 is less than a depth (D) of the mold 22.

The method further comprises placing a first liquid comprising the first phase-separated polymer and the active agent in the mold 22. The first liquid may further comprise a solvent. When the first liquid includes a solvent, the first liquid is typically formed by dissolving the first phase-separated polymer and the active agent in the solvent. Of course, the spacer 26 and the first liquid may be placed in the mold 22 in any order. When in the mold 22, the first liquid and the spacer 26 are in contact. In other words, the spacer 26 displaces at least a portion of the volume of the first liquid in the mold 22.

The method further comprises cooling the first liquid to freeze the first liquid. The cooling of the first liquid may be carried out at any suitable temperature capable of freezing the first liquid.

Figure 9:
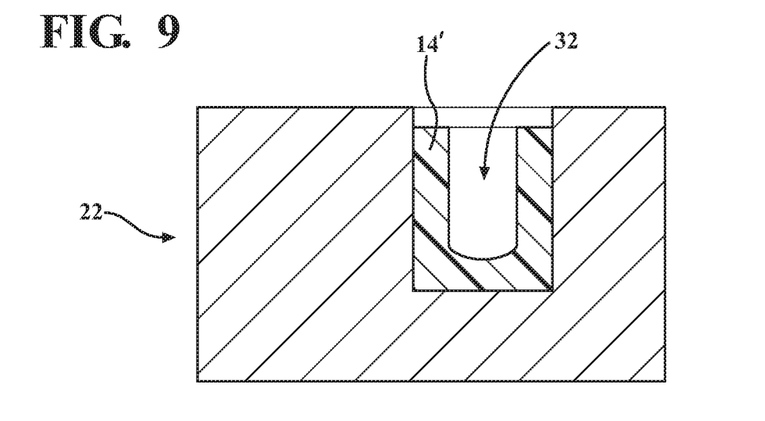
FIG. 9 is a cross-sectional view of the mold of FIG. 8 including a frozen first liquid.

The method further comprises removing the spacer 26 from the frozen first liquid to expose a cavity 32 in the frozen first liquid. For example, as shown in FIG. 9, the cavity 32 of the frozen first liquid is complementarily shaped as the protrusion 30 of the spacer 26. It is to be appreciated that the frozen first liquid may also be referred to as a frozen shell portion 14'. To facilitate removal of the spacer 26 from the frozen first liquid, the spacer 26 is typically formed of PTFE and generally cylindrically shaped. PTFE is advantageous due to its inherent low frictional properties. In addition, using a generally cylindrically shaped spacer 26 allows the spacer 26 to be "spun" while being removed to loosen the spacer 26 from the frozen first liquid without disrupting the physical shape of the frozen first liquid. A void volume of the mold 22 may also have a generally square cross-sectional shape, which is advantageous in preventing the frozen first liquid from also being spun simultaneously with the spacer 26. Of course, the spacer 26 and mold 22 may be formed from any suitable material and be any suitable geometric configuration.

The method further comprises placing a second liquid in the cavity 32 of the frozen first liquid. The second liquid comprises a second phase-separated polymer that is the same as or different than the first phase-separated polymer. The second liquid may optionally include an active agent (e.g. a hemostatic agent) and a solvent.

Figure 10:
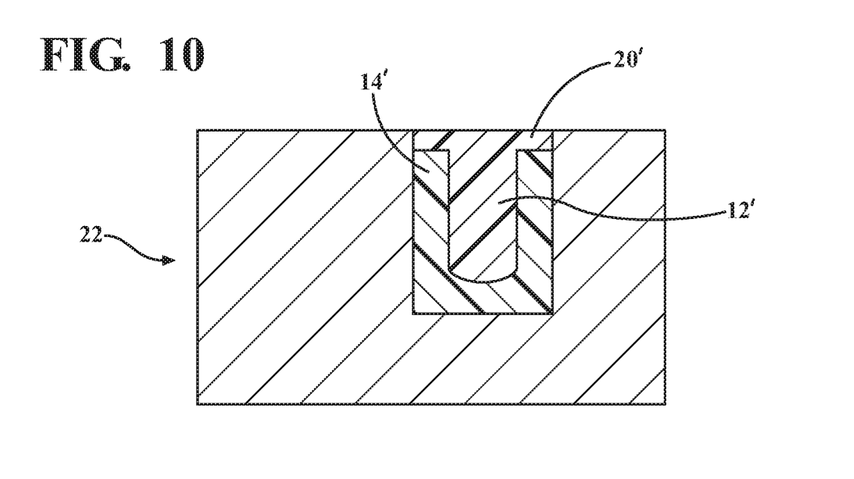
FIG. 10 is a cross-sectional view of the mold of FIG. 9 further including a frozen second liquid.

The method further comprises cooling the second liquid to freeze the second liquid. Cooling of the second liquid may also be carried out any suitable temperature capable of freezing the second liquid. As best shown in FIG. 10, freezing the second liquid may produce a frozen core portion 12' and a frozen base portion 20' with the frozen core portion 12' entirely disposed within the frozen shell portion 14'. In addition, the frozen shell portion 14' and frozen base portion 20' may cooperate to encapsulate the frozen core portion 12'.

The method further comprises drying the first and second frozen liquids to form the foam nasal dressing 10 including the foamed core portion 12' at least partially disposed within the foamed shell portion 14'. In other words, the drying the frozen first liquid forms the foamed shell portion 14' and drying the frozen second liquid forms the foamed core portion 12'. Suitable methods of forming, cooling, and drying the first and second liquids are described in U.S. Pat. App. Pub. No. 2015/0320901, which is incorporated by reference in its entirety.

In certain examples, drying is performed by lowering the pressure and increasing the temperature such that any solvent present in first and second frozen liquids is sublimed from the phase-separated polymers. In some examples, the temperature increase may be in part from the latent heat of sublimation of solvent molecules and may result in up to 90%, 95%, or 100% of the solvent subliming. The entire freeze-drying process may last from about 1 hour to 24 hours, or more. Typically, the entire freeze-drying is performed for a period of about 15 hours.

In certain examples, the placing the second liquid in the cavity 32 of the frozen first liquid is further defined as overflowing the cavity 32 of the frozen first liquid with the second liquid. When the cavity 32 is filled in this manner, after the method is complete, the "over flow" may form the foamed base portion 20'. Accordingly, in these examples, the foamed core portion 12' and the foamed base portion 20' have the same chemical composition, porosity, foam density, and are integral. In addition, the foamed core portion 12' and the foamed shell portion 14' extend from the foamed base portion 20'.

In certain examples, the method further includes placing a third liquid in the mold 22 after the cooling of the first and second liquids but before drying the first and second frozen liquids. In these examples, the third liquid includes the third phase-separated polymer and optionally includes a solvent and an active agent. In these examples, the third liquid is frozen and subsequently dried along with the first and second frozen liquids to form the foam nasal dressing 10 including the foamed base portion 20'.

When solvent is included in the first, second, and/or third liquids suitable solvents include polar solvents which have freezing points in the range of about 0-50° C. Such solvents may be removed by drying. Such suitable solvents include organic solvents such as acetic acid, benzene, cyclohexane formic acid, nitrobenzene, phenol, 1,4-dioxane, 1,2,4-trichlorobenzene, dimethylsulphoxide (DMSO) and combinations thereof. In one example, the solvent used is 1,4-dioxane.

In certain examples, when the active agent is not soluble in the phase-separated polymer or solvent, the method comprises additional steps to ensure a homogeneous incorporation of the active agent into the particular foam portion. When the active agent is not soluble in the phase-separated polymer and/or solvent, the active agent is typically a particle. These additional steps are described in U.S. Pat. No. 9,422,389, which is incorporated by reference in its entirety.

In one example, homogenous incorporation is achieved by carrying out the cooling step such that the temperature of the first and/or second liquid is decreased below the freezing point (crystallization temperature) of the liquid at a high rate, typically within 10 s.

These cooling rates will depend on the type of solvent or solvents that are used and the speed at which it is possible to sublimate the solvent or solvents from the foam using the drying process. When the temperature of the polymer/particles mixture is lower than the freezing point (crystallization temperature) of the solvent or solvents, the solvent crystallizes. Subliming the solvent or solvents results in a foam comprising a homogeneous distribution of particles.

In a particular example, the first and/or second liquid is frozen within 60 seconds (s) and subsequently subliming the one or more solvents to form the foam comprising a homogenous distribution of particles.

In another alternative example, a homogeneous incorporation of particles into a foam may also be achieved by cooling the first and/or second liquid to freeze the first and/or second liquid and subsequently increasing the temperature at least once above the freezing point of the one or more solvents to melt the partly frozen phase-separated polymer/particles mixture and decreasing the temperature to re-freeze the phase-separated polymer/particles mixture; and subsequently drying the frozen first and second liquids by sublimation of the one or more solvents to form a foam comprising a homogenous distribution of particles.

The size of the particle used also affects their distribution within the foam. The use of ultrafine particles in the process leads to a good particle distribution throughout the foam and minimizes particle aggregation. The use of larger sized particles, however, is less desirable since this can lead to an increased possibility of coagulation or agglomeration of the particles in the foam. The coagulation of particles in the foam is can result in the foams becoming brittle which would make them unsuitable for use.

The particles are preferably solid. Suitable solid particles to be used are insoluble and hydrophilic and may be organic, inorganic or a mixture of both. The particle size is typically from 1-1000 µm, preferably 1-150 µm and even more preferably 15-120 µm. The particles may be any suitable shape but are preferably roughly spherical.

Particles may be anti-clotting agents, anti-bacterial agents, anti-fungal agents, antiseptics or other suitable drugs. Preferably the particles may be smooth particles about 20-30 µm in size or rough particles about 60-115 µm in size.

In addition to forming a homogeneous distribution of the insoluble drug in the particular foamed portion, it is also possible to form a layer of the insoluble drug in the particular foamed portion. In these examples, the cooling the first or second liquid to the freezing point of one or more solvents including therein within 60 s to 600 s; and subsequently drying the polymer/particles mixture by the sublimation of the one or more solvents to form a foam comprising one or more layers of particles. In these examples, the particles are typically lighter than the solvent or solvents and do not rise to the top as one would expect, instead the particles form a layer underneath the foam.

In a first non-limiting example, a method for forming the foam nasal dressing 10 is provided. The method comprises providing the mold 22. The method also comprises placing the spacer 26 and a first liquid in the mold 22, such that the first liquid and spacer 26 are in contact in the mold 22. The first liquid comprises the first phase-separated polymer, e.g. first polyurethane, and the active agent, e.g. a steroid. The method further comprises cooling the first liquid to freeze the first liquid and removing the spacer 26 from the frozen first liquid to expose the cavity 32 in the frozen first liquid. The method further comprises placing a second liquid in the cavity 32 of the frozen first liquid. The second liquid comprises the second phase-separated polymer, e.g. second polyurethane, that is the same as or different than the first phase-separated polymer (and optionally a chitosan hemostatic agent). The method further comprises cooling the second liquid to freeze the second liquid. The method further comprises drying the first and second frozen liquids to form the foam nasal dressing 10 comprising the foamed core portion 12 at least partially disposed within the foamed shell portion 14.

Figure 11:
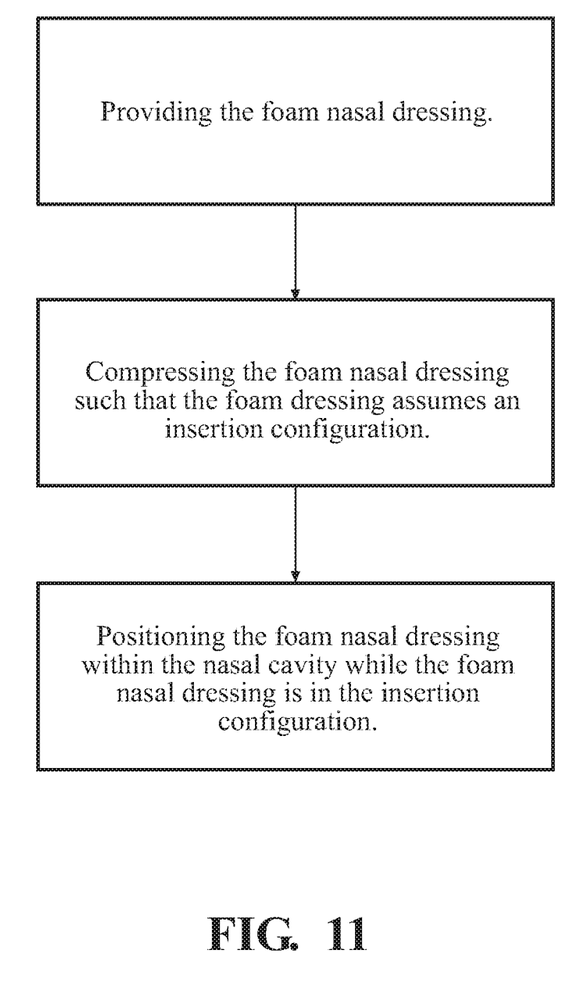
FIG. 11 is a flow diagram illustrating steps included in a method of simultaneously treating inflammation and absorbing fluid discharge from the sinus cavity with the foam nasal dressing.

Referring now to FIG. 11, a method of simultaneously treating inflammation and absorbing fluid discharge from the sinus cavity with the foam nasal dressing 10 is also disclosed. The method comprises the steps of providing the foam nasal dressing 10, compressing the foam nasal dressing 10 such that the foam dressing assumes an insertion configuration, and positioning the foam nasal dressing 10 within the nasal cavity while the foam nasal dressing 10 is in the insertion configuration such that the second end 18 of the foam nasal dressing 10 is farther from the user than the first end 16. In the method, the foam nasal dressing 10 is just as described above.

The steps compressing the foam nasal dressing 10 such that the foam dressing assumes an insertion configuration, and positioning the foam nasal dressing 10 within the nasal cavity while the foam nasal dressing 10 is in the insertion configuration such that the second end 18 of the foam nasal dressing 10 is farther from the user than the first end 16 can be accomplished via hand, with various types of forceps known to those skilled in the art, or with other instruments known in the art or developed specifically for the foam nasal dressing 10.

The method of simultaneously treating inflammation and absorbing fluid discharge from the sinus cavity with the foam nasal dressing 10 could utilize the foam nasal dressing 10 comprising the foamed core portion 12 and the foamed shell portion 14 arranged such that the foamed core portion 12 is at least partially disposed within the foamed shell portion 14. The foamed core portion 12 could comprise a first polyurethane including amorphous segments and crystalline segments, the crystalline segments formed via hydrogen bonding, and have the hemostatic agent, e.g. chitosan, disposed therein. The hemostatic agent could include at least one hydrogen atom bonded to a nitrogen atom, and at least one hydrogen atom bonded to an oxygen atom, the hydrogen atoms being available to form a hydrogen bond with the crystalline segments of the first polyurethane foam. The foamed shell portion 14 could have a porosity of greater than 80% and comprise a second polyurethane including amorphous segments and crystalline segments, the crystalline segments formed via hydrogen bonding. In this example, the first and second polyurethanes are the same or different. In this example, the hemostatic agent may be disposed in the foamed core portion 12 and or/the foamed shell portion 14, and the steroid may be disposed in the foamed core portion 12 and or/the foamed shell portion 14. As previously described, the foam nasal dressing 10 of this example may have an elongate shape extending from a first end 16 to a second end 18, with a first half adjacent the first end 16 and a second half adjacent second end 18. The weight of a drug in the first half of the foam nasal dressing 10 is, in many examples, greater than a weight of the drug in the second half of the foam nasal dressing 10.

One or more of the values described above may vary by ±5%, ±10%, ±15%, ±20%, ±25%, etc. so long as the variance remains within the scope of the disclosure. Each member may be relied upon individually and or in combination and provides adequate support for specific examples within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

All combinations of the aforementioned examples throughout the entire disclosure are hereby expressly contemplated in one or more non-limiting examples even if such a disclosure is not described verbatim in a single paragraph or section above. In other words, an expressly contemplated example may include any one or more elements described above selected and combined from any portion of the disclosure.

It is also to be understood that any ranges and subranges relied upon in describing various examples of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various examples of the present disclosure, and such ranges and subranges may be further delineated into relevant halves, thirds, quarters, fifths, and so on. As just one example, a range "of from 0.1 to 0.9" may be further delineated into a lower third, i.e. from 0.1 to 0.3, a middle third, i.e. from 0.4 to 0.6, and an upper third, i.e. from 0.7 to 0.9, which individually and collectively are within the scope of the appended claims, and may be relied upon individually and/or collectively and provide adequate support for specific examples within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific examples within the scope of the appended claims. Finally, an individual number within a disclosed range may be relied upon and provides adequate support for specific examples within the scope of the appended claims. For example, a range "of from 1 to 9" includes various individual integers, such as 3, as well as individual numbers including a decimal point (or fraction), such as 4.1, which may be relied upon and provide adequate support for specific examples within the scope of the appended claims.

Several examples have been discussed in the foregoing description. However, the examples discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

What is claimed is:

1. A foam nasal dressing for topically administering a drug to a nasal cavity and for absorbing fluid discharge, the nasal dressing comprising:
    a foamed core portion comprising a first polyurethane, the foamed core portion including amorphous segments and crystalline segments, and a hemostatic agent;
    a foamed shell portion arranged such that the foamed core portion is disposed within the foamed shell portion, the foamed shell portion having a porosity of greater than 80% and comprising a second polyurethane, the foamed shell portion including amorphous segments and crystalline segments, wherein the first and second polyurethanes are the same or different;
    a drug disposed in the foamed shell portion;
    the nasal dressing having an elongate shape extending from a first end to a second end, the nasal dressing having a first half adjacent the first end and a second half adjacent the second end; and
    a foamed base portion at the second end with the foamed shell portion and the foamed core portion extending from the foamed base portion towards the first end, such that the foamed base portion and the foamed shell portion cooperate to encapsulate the foamed core portion and define an outer surface of the nasal dressing;
    wherein a weight of the drug in the first half of the foam nasal dressing is greater than a weight of the drug in the second half of the foam nasal dressing; and wherein the foamed base portion comprises the first polyurethane and is integral with the foamed core portion.

2. The foam nasal dressing as set forth in claim 1, wherein the drug comprises a steroid, and wherein the foamed shell portion includes the steroid, and the foamed core portion is substantially free of the steroid.

3. The foam nasal dressing as set forth in claim 2, wherein the steroid includes at least one hydrogen atom which is bound to a nitrogen, oxygen, or fluorine atom.

4. The foam nasal dressing as set forth in claim 1, wherein the foamed shell portion and the foamed core portion are bonded to one another via hydrogen bonding and substantially free of covalent bonds therebetween.

5. The foam nasal dressing as set forth in claim 1, wherein:
the crystalline segments in the first and/or the second polyurethane comprise the reaction product of 1,4 butanediol and 1,4 diisocyanatobutane; and/or
wherein molecules within the first and/or second polyurethane foam are arranged so that the crystalline segments and the amorphous segments stack in an alternating configuration to provide a 3-dimensional porous structure which is strengthened via hydrogen bonding between the stacked crystalline segments.

6. The foam nasal dressing as set forth in claim 1, wherein the foamed core portion includes the drug at a first concentration, and the foamed shell portion includes a second drug, which is the same as or different than the drug, at a second concentration.

7. The foam nasal dressing as set forth in claim 1, wherein the foamed core portion and/or the foamed shell portion comprise a hemostatic agent.

8. The foam nasal dressing as set forth in claim 7, wherein the hemostatic agent includes at least one hydrogen atom bonded to a nitrogen atom, and at least one hydrogen atom bonded to an oxygen atom.

9. The foam nasal dressing as set forth in claim 8, wherein molecules of the hemostatic agent and molecules of the second polyurethane foam are bonded to one another via hydrogen bonding and substantially free of covalent bonds therebetween.

10. The foam nasal dressing as set forth in claim 7, wherein the hemostatic agent is insoluble in the first and/or second polyurethane foam and the drug is a steroid that is insoluble in the first and/or second polyurethane foam.

11. The foam nasal dressing as set forth in claim 1, wherein the foam dressing is free from any lumen.

12. The foam nasal dressing as set forth in claim 1, wherein a volume of the foamed shell portion is from about 20 to about 40% of a total volume of the foam nasal dressing and/or wherein the foamed core portion has a porosity of greater than 80%.

13. The foam nasal dressing as set forth in claim 1, wherein:
the foamed core portion is completely disposed within the foamed shell portion;
the foamed core portion is cylindrically-shaped; and/or
a cross-section of the foamed shell portion has a square or rectangular shape and is the same shape as a cross-section of the foamed base portion.

* * * * *